United States Patent
Eggenberger-Wang et al.

(10) Patent No.: US 8,533,005 B2
(45) Date of Patent: Sep. 10, 2013

(54) METHOD AND SYSTEM FOR OPTIMIZING UTILIZATION OF A DONOR

(75) Inventors: Christian Eggenberger-Wang, Wil (CH); Peter K. Malkin, Ardsley, NY (US); Jueng von Kaenel, Mahopaca, NY (US); Andre Zgraggen, Mettmenstetten (CH)

(73) Assignee: International Business Machines Corporation, Armonk, NY (US)

( * ) Notice: Subject to any disclaimer, the term of this patent is extended or adjusted under 35 U.S.C. 154(b) by 1320 days.

(21) Appl. No.: 11/676,825

(22) Filed: Feb. 20, 2007

(65) Prior Publication Data

US 2008/0201167 A1    Aug. 21, 2008

(51) Int. Cl.
*G06Q 10/00* (2012.01)
(52) U.S. Cl.
USPC .................................................. 705/2; 705/3
(58) Field of Classification Search
USPC .......................................................... 705/2
See application file for complete search history.

(56) References Cited

U.S. PATENT DOCUMENTS

| | | | | |
|---|---|---|---|---|
| 5,551,880 A | * | 9/1996 | Bonnstetter et al. | 434/236 |
| 6,358,201 B1 | * | 3/2002 | Childre et al. | 600/300 |
| 6,675,130 B2 | * | 1/2004 | Kanevsky et al. | 702/188 |

OTHER PUBLICATIONS

Karina Oertel, et al., "EmoTetris for Recognition of Affective States", Fraunhofer Institute for Computer Graphics Rostock, Department of Human-Centered Interaction Technologies, pp. 1-10.
Rollin McCraty, et al., "Science of the Heart", Exploring the Role of the Heart in Human Performance, 2001 Institute of HeartMath, pp. 1-70.
Jamie Milne, "Where do you wear your thinking cap?", Guardian Newspapers Limited 2005, pp. 1-3.
BW Online Polls, "What percentage of your workday do you spend doing things you like to do?", The McGraw-Hill Companies Inc. 2000-2005, pp. 1-2.

* cited by examiner

*Primary Examiner* — Michael Fuelling
(74) *Attorney, Agent, or Firm* — Vazken Alexanian; McGinn IP Law Group, PLLC (57) ABSTRACT

A system (and method) for optimizing utilization of a human resource, including determining an emotional state or a physical state of the human resource, and determining whether the emotional state or the physical state of the human resource corresponds to a task.

9 Claims, 11 Drawing Sheets

| Task ID | Work Location | SLA | Current SL | Required Skills | Number of Donors | Job Length | Task Complete |
|---|---|---|---|---|---|---|---|
| ... | ... | | ... | ... | ... | | ... |
| ... | ... | | ... | ... | ... | | ... |
| ... | ... | | ... | ... | ... | | ... |
| 321 | India | Gold | Silver | Java, JSP | 30 | 6 months | No |

Figure 7

| User ID 8010 | Blood Pressure 8020 | Pulse (bps) 8030 | Mood 8040 | Level of Fatigue 8050 | Acceptable Locations 8060 | Skills 8070 | Task ID 8080 | SL Rating 8090 |
|---|---|---|---|---|---|---|---|---|
| | | | | | | | | |
| | | | | | | | | |
| | | | | | | | | |
| 40960 8100 | 110/80 8110 | 70 8120 | 8 8130 | 2 8140 | US, India, UK 8150 | Java, JSP, REXX 8160 | 321 8170 | Bronze 8180 |

METHOD AND SYSTEM FOR OPTIMIZING UTILIZATION OF A DONOR

BACKGROUND OF THE INVENTION

1. Field of the Invention

The present invention generally relates to a system and method for optimizing the utilization of human resources. More particularly, the present invention relates to a method and system for optimizing the utilization of human resources according to emotional and physical states.

2. Description of the Related Art

It has been said that e-business is not about technology—it is about how business is being transformed. The same is true for e-business on demand. The extension expresses the growing need of organizations to act highly agile in an increasingly dynamic and global market. Autonomic, Grid and Utility Computing are important underlying technical concepts for an agile on demand business.

These are hard facts, but the problem is the role of the human being in such a business centric view.

The General Assembly of the United Nations constitutes in the Universal Declaration of Human Rights that:

Article 23—Everyone has the right to work, to free choice of employment, to just and favorable conditions of work and to protection against unemployment. Everyone, without any discrimination, has the right to equal pay for equal work.

Article 24—Everyone has the right to rest and leisure, including reasonable limitation of working hours and periodic holidays with pay.

The world economic leaders push globalization with the goal to improve the welfare of all human beings with adequate political, social and economical measures.

Also entrepreneurs claim that a good work-life balance of the employees is crucial, because they are, with their workforce, skills and experience, the most important asset.

However, the on demand requirements of an increasing dynamic global marketplace and the right to work to just and favorable conditions are in opposition if human beings are not empowered to work on demand.

SUMMARY OF THE INVENTION

In view of the foregoing and other exemplary problems, drawbacks, and disadvantages of the conventional methods and structures, an exemplary feature of the present invention is to provide a method and structure in which utilization of a donor is optimized according to a state (emotional and/or physical) of that donor.

In a first exemplary aspect of the present invention, a method for optimizing utilization of a human resource includes determining an emotional state or physical state of a human resource, and determining whether the emotional state or the physical state of the human resource corresponds to a task.

In a second exemplary aspect of the present invention, a system for optimizing utilization of a human resource, includes a human resource state handler that determines an emotional state or physical state of the donor, and a human resource compatibility handler that determines whether the emotional state or the physical state of the human resource corresponds to a task.

In a third exemplary aspect of the present invention, a system for optimizing utilization of a human resource, includes means for determining an emotional state or a physical state of the donor, and means for determining whether the emotional state or physical state of the human resource corresponds to a task.

In the recent years after the e-business bubble burst, the inventors discovered in the consulting environment that human beings with appropriate capabilities are not as smoothly available as requested. The inventors made the following observations:

A too high percentage of highly educated employees were sitting "on the bench" endangered to lose their jobs and, therefore, executing work which was not appropriate for their skill and salary levels.

In some high on demand areas too few people had the required capabilities and were constantly over-utilized. But, oftentimes, businesses were not allowed to hire or allocate human beings having the required capabilities, because the middle- or long-term business outlook did not look bright enough to allow such a "permanent" move. Sometimes the management policies were too rigid to respond to a single case.

The inventors observed that employees needed support from colleagues with specific skills for a short period who were not available within their division or their region. But the processes for allocating support from those colleagues were too time consuming to allocate people with very specific skills for a rather small task which needs immediate attention.

It quite often requires too much effort and time to leverage the capabilities of human beings who become part of a merger, acquisition, or an outsourcing deal, because the new employer is not able to quickly overview the vast amount of acquired intrinsic and extrinsic capabilities. The risk continues to increase that people with a high market value leave a company even though that company needs to utilize the new colleagues with their specific capabilities.

The inventors also observed that brainworkers cannot burden their brain with highly complex tasks for a long period without decreasing performance. They need relief by doing, for a limited time, something different which has a more routine character and which requires a different brain part. For example, the inventors encountered brainworkers under high pressure who sighed when they saw a postman crossing the street that from time to time they would like to do a more routine job outdoor combined with more physical capabilities or to leverage more physical capabilities.

The inventors also observed that routine workers pine for a restricted change to experience something new, explore hidden strengths or contribute additional value by bringing in their know how and passion they live out in their hobbies.

An intellectual capital management system should leverage employees in a manner which reuses intellectual capital in an efficient and effective way. This is often theory, because many valuable documents are accessible in a language the recipient or the client does not understand. On the other hand, the contributor does not have the skills, the time or the incentive to provide his intellectual capital in the required language.

The tangible know how stored in databases is only the peak of the iceberg. The real, intangible know how is still in the heads and souls of the people and can only by accessed by communicating directly with them.

These drawbacks of the conventional systems within many corporations and the increasing cost and value pressure from the market side has caused much agony.

Against this backdrop, the inventors had an inspiration. One reason for using grid computing models is to exploit underutilized resources. The inventors discovered that a great advantage could be realized by a system and method that accounts for whether a person is under-stimulated or over-stimulated and, as such, whether that person would be balanced into an ideal stimulation zone by a grid computing model which imbeds the person as a central resource.

Conventional grid computing is an advanced distributed computing model which leverages the computing capabilities of the infrastructure in contrast to a model that is based on discrete infrastructure components. The goal is to create a simple yet large and powerful self-managing virtual computer out of a large collection of connected heterogeneous systems sharing various combinations of resources.

An exemplary embodiment of the present invention goes beyond the pure hard- and software-based conventional grid computing model by imbedding human beings as an additional extremely important resource whose unique capabilities are leveraged.

Conventional human resource allocation systems may include a scheduler which decomposes a task into subtasks and then allocates the subtasks to distributed human resources. The human resources each including one or more humans. For the purpose of the present application, those of ordinary skill in the art understand that the terms "humans," "persons," "donors," "nodes," "resources," "members," "clients," "hosts," "engines," "agents" and the like may be used synonymously with the term "human resources."

A conventional scheduler assigns human resource to subtasks in an attempt to ensure that all subtasks are performed in a given time to a required quality. In case one of the human resources fails to accomplish the assigned subtask, then the scheduler re-allocates the subtask to another available human resource. The inventors discovered that these conventional systems and methods fail to adequately assign human resources to accomplish tasks because the conventional systems and methods do not account for the emotional and physical states of the human resources. In other words, these conventional methods and systems treat the human resources as machines and not as humans.

An exemplary embodiment of the present invention monitors the somatic (i.e. physical) and affective (i.e. emotional) states of human resources and determines an optimal allocation of the human resources to tasks.

An exemplary embodiment of the present invention may track the emotional and physical states of human resources around the clock in order to constantly determine the capacity of the human resources and maintain those human resources within a preferred set of emotional and physical states. For example, this embodiment may allocate tasks to human resources in such a manner that the human resources are maintained in a happy emotional state and in good physical condition.

An exemplary system and method of the present invention optimizes the utilization of human resources Within an exemplary embodiment of the present invention, a human resource may bestow his capabilities and passion to accomplish a job that is allocated by a scheduler depending on the current affective and somatic state of the human resource, specific preferences, restrictions, availability, utilization degree of the human resource and the like.

An exemplary embodiment of the present invention relies upon the somatic state of the human resource. The somatic state is one variable to estimate the human resource's physical condition by measuring, for example, the level of blood sugar, the blood heat, or the like.

An exemplary embodiment of the present invention relies upon the affective state of a human resource. The affective state is another variable to detect a human resource's mood to perform a job with lust, joy or any other emotional condition. Basic emotions may include, for example, states of fear, anger, joy, sadness, disgust, seeking/curiosity, social distress, lust, care, play, and the like. Certain emotional conditions have noticeable and measurable physiological correlates. Depending upon the intensity of the emotions, these may include changes in autonomic functions, such as, for example, heart rate, blood pressure, respiration, sweating, trembling, and other features like hormonal changes; changes in body temperature; and changes in neural function that are measurable.

In an exemplary embodiment of the present invention, the emotional and physical states may be sensed via non-invasive biosensors which may be embedded in, for example, wearable jewelry, clothing designs and gloves. In an exemplary embodiment of the present invention bio-signals may be transmitted across the body by using the natural electrical conductivity of the human body and wirelessly transferred to near-off body locations.

In exemplary embodiment of the present invention a human resource may self-assess his affective and somatic state or could make the decision "what he wants to do" with or without support of information gathered from biosensors.

Most human beings have preferences about the kind of work they would like to perform, but conventionally cannot fully satisfy them in their current job role for several reasons, for example: 1) a task may not be the core focus of their work unit; 2) the preferences of the human resource changed over time, but the human resource did not have a real alternative to find a new appropriate position internally; 3) the human resource's preferences, which were originally congruent, diverged more and due to organizational adjustments; or 4) the human resource likes his job function overall but would like to explore his hidden capabilities once in a while.

In an exemplary embodiment of the present invention a human resource publishes and nurtures his preferences via a database. For privacy or security reasons this information may be anonymous. This repository may store information to determine whether a job matches the preferences of a human resource.

Similarly, in an exemplary embodiment of the present invention, a human resource may impose restrictions. For example, a human resource may impose restrictions that are designed to prevent the human resource receiving job requests that the human resource cannot or does not want perform.

An exemplary embodiment of the present invention includes a scheduler that checks, via calendar tools, the availability of a donor before it transmits a job request to the donor. The check could, for instance, clarify that the donor has enough time available to finish the job if there is a time constraint by the requester.

An exemplary embodiment of the present invention distinguishes between a human resource that may be fully available for task allocation and a human resource which may only be available on a limited basis. For example, a human resource may be required to fulfill utilization targets in their core activity and these core activities should not be jeopardized by the allocation of other tasks to these human resources. The scheduler in this exemplary embodiment assists the human resource in staying on track with that human resource's utilization targets.

These and many other advantages may be achieved with the present invention.

BRIEF DESCRIPTION OF THE DRAWINGS

The foregoing and other exemplary purposes, aspects and advantages will be better understood from the following detailed description of an exemplary embodiment of the invention with reference to the drawings, in which.

DETAILED DESCRIPTION OF EXEMPLARY
EMBODIMENTS OF THE INVENTION

Referring now to the drawings, and more particularly to FIGS. 1-11, there are shown exemplary embodiments of the method and structures of the present invention.

Figure 1:
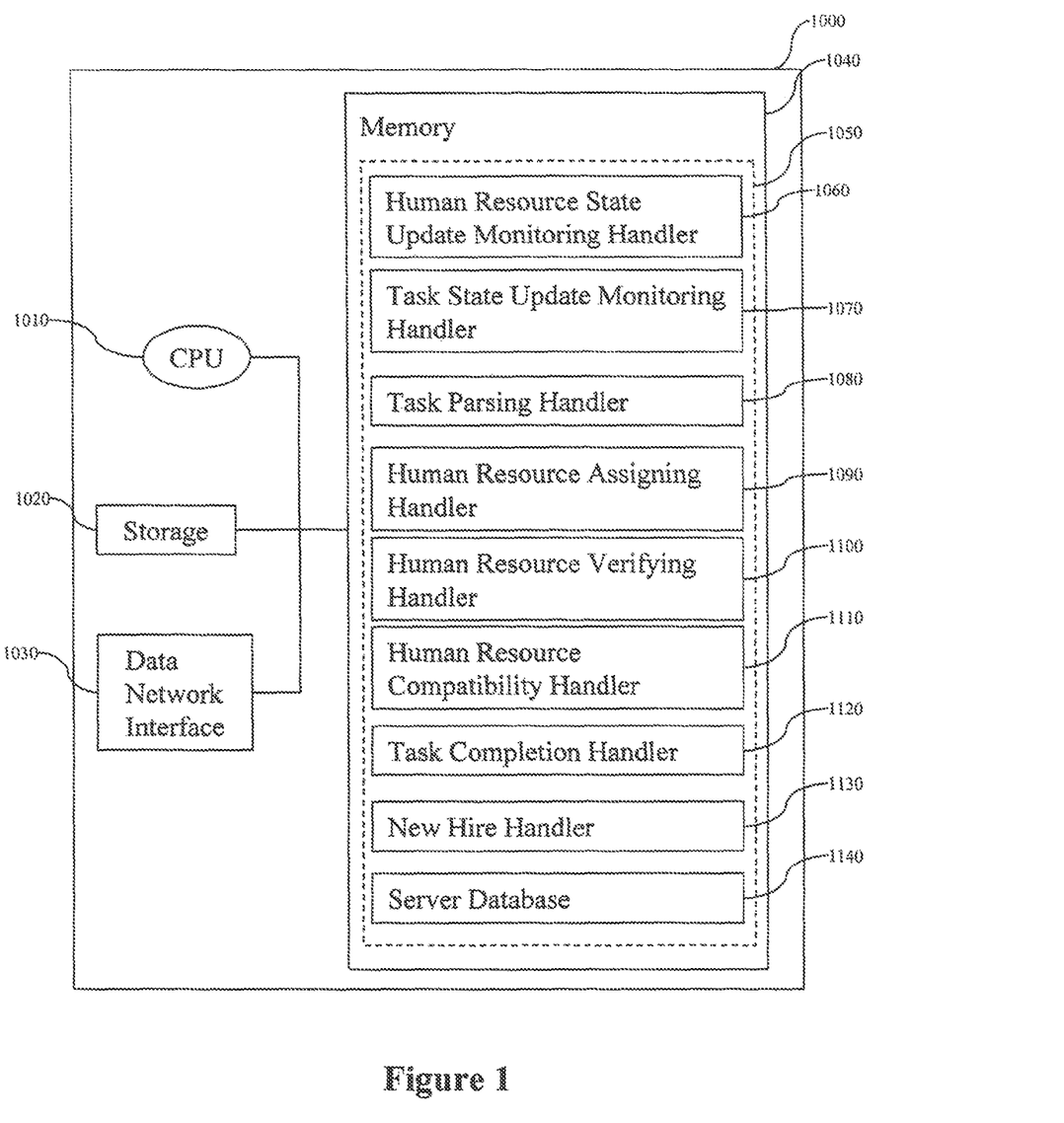
FIG. 1 illustrates an exemplary system 1000 for optimizing utilization of human resources in accordance with the present invention.

FIG. 1 illustrates an exemplary system 1000 for optimizing the utilization of human resources in accordance with the present invention. The system 1000 provides the current invention, including description of how it enables the assignment of human resource to a given task based not only on their skills and availability, but also on their affective (emotional) and somatic (physical) state. Both of these states will be described in detail with reference to FIGS. 1-2, 5, and 7-8.

The system 1000 may include any computing node that is able to load and execute programmatic code, including, but not limited to: products sold by IBM such as ThinkPad® or PowerPC®, running the operating system and server application suite sold by Microsoft, e.g., Windows® XP, or a Linux operating system. System logic 1050 is embodied as computer executable code that is loaded from a remote source (e.g., from a network file system), local permanent optical (CD-ROM), magnetic storage (such as disk), or storage 1020 into memory 1040 for execution by CPU 1010.

As will be discussed in greater detail below, the memory 1040 includes computer readable instructions, data structures, program modules and application interfaces forming the following components: a donor state update monitoring handler 1060, a task state update monitoring handler 1070, a task parsing handler 1080, a human resource assigning handler 1090, described in detail below with reference to FIG. 4, a human resource verifying handler 1100, described in detail below with reference to FIG. 5, a human resource compatibility handler 1110, described in detail below with reference to FIG. 6, a task completion handler 1120, described in detail below with reference to FIG. 3, a new hire handler 1130, described in detail below with reference to FIG. 9, and a server database 1140.

The human resource state update monitoring handler 1060 monitors all updates concerning a given human resource's state. This includes the human resource's affective or emotional state, somatic or physical state, abilities (e.g., type of skills, level of skill, rating of expected level of performance), and availability (e.g., are they now free, and for how long). All such human resource state information is stored in the server database 1140, and will be described in detail below with references to FIG. 8. This handler 1060, once started, runs continuously on the server 1000.

Sources for updates to this handler 1060 include, for example, network feeds of affective and somatic state date provided by non-invasive sensors worn by donors, such updates possible being provided constantly (7 by 24). Human resources may also routinely connect themselves to measurement equipment (e.g., devices located at a given user's home or work) and have this equipment determine their current data and then send it to the handler 1060. In addition, a human resource may also determine one or more data values for themselves (e.g., their current mood) and then communicate this value to the handler 1060 (e.g., via a web service).

Figure 8:
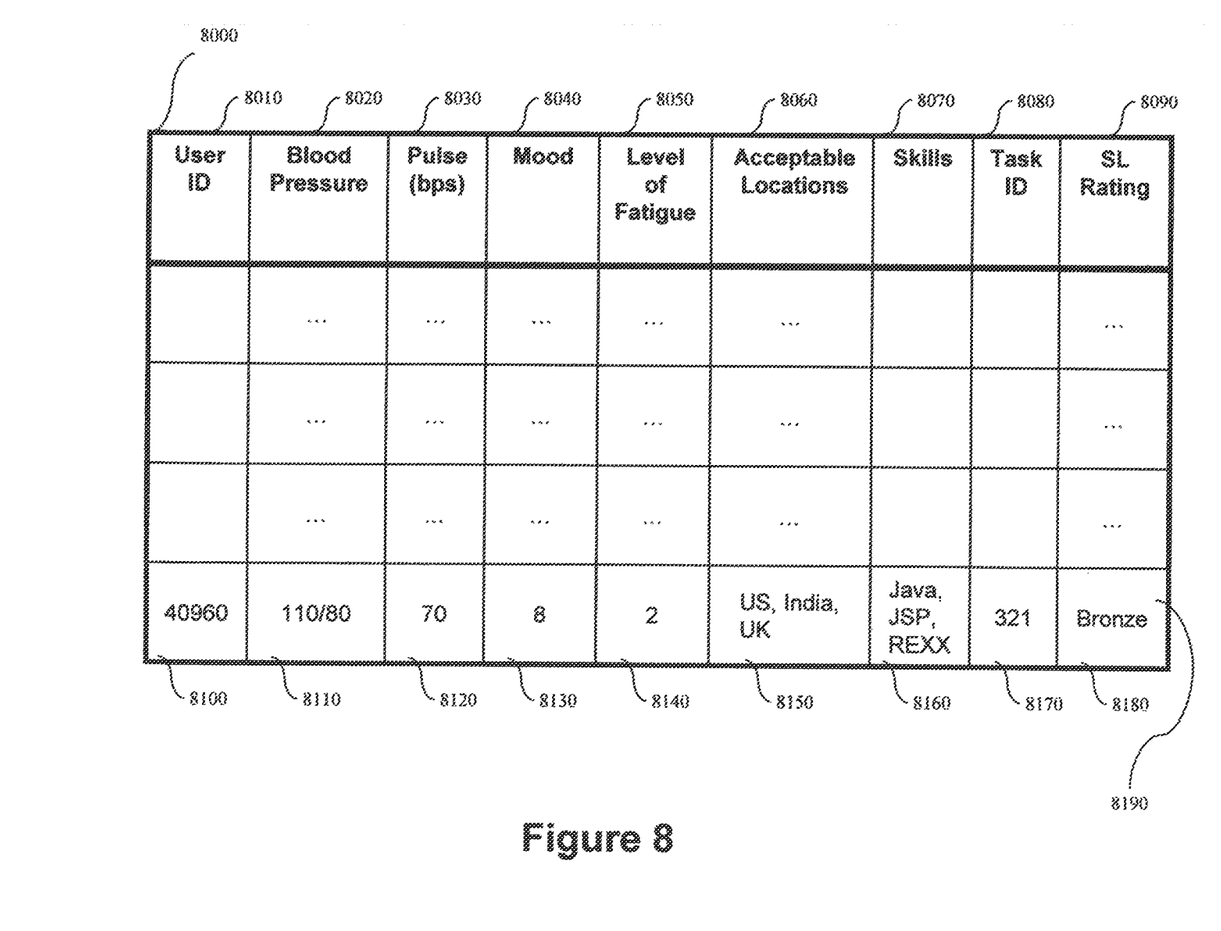
FIG. 8 is a table 8000 of human resource states in accordance with an exemplary embodiment of the present invention.

Those of ordinary skill in the art will appreciate that the state update monitoring handler 1060 can also employ usage patterns as a source of its updates. For example, the state update monitoring handler 1060 could check whether a human resource's performance level consistently dropped whenever they worked in a particular location. Given this data, the handler 1060 could infer that the human resource was not able to work effectively in that given location, and so, in response, delete the given location from the list 8060 of locations that are acceptable to the human resource. Those of ordinary skill in the art further appreciate that this performance tracking could be accomplished by maintaining a log of human resource's performance levels and active location for every task.

The task state update monitoring handler 1070 is responsible for monitoring and updating the state of any and all tasks being managed by the server 1000. As will be described in detail below with reference to FIG. 7, this data can include such things, such as, for example, the current level of service being provided to a given task or whether a given task has been completed. Just as with the human resource state update monitoring handler 1060, this handler 1070 runs continuously once started, capturing task-related state information and it updates the task state information held in the server database 1140, this state information described in detail below with reference to FIG. 7.

Figure 7:
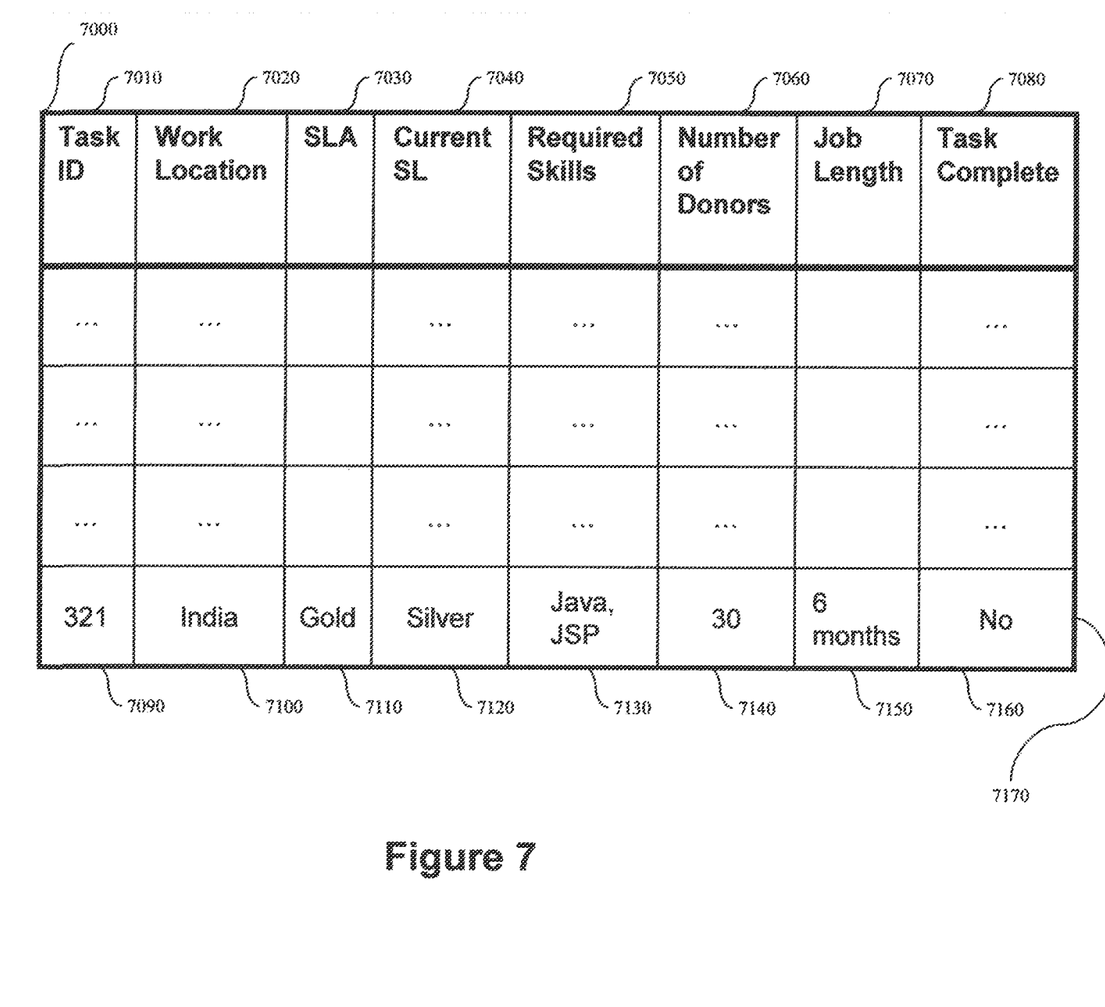
FIG. 7 is a table 7000 of task specifications in accordance with an exemplary embodiment of the present invention.

In addition to a push communications model, e.g., where data is actively sent to a handler (1060 or 1070), the current invention also encompasses embodiments where, for example, either the human resource state update monitoring handler 1060 or the task state update monitoring handler 1070 obtains data using a pull communication model, e.g., where the handler queries or polls for one or more data values. Examples include a case where the donor state update monitoring handler 1060 periodically queries the human resources that it is tracking for their list of acceptable work locations 8060, or where the task state update monitoring handler 1070 polls a remote data source to determine whether any of the tasks that is tracking have been completed 7080. This polling could include making a network socket connection to an application running on the remote source and then sending the remote source the task IDs 7010 of each of the relevant task and then checking the value returned by the remote source.

The term compatible indicates that a human resource may be, for example, available, adequate (skill and quality of performance), in a sufficient somatic (physical) state, and/or in a sufficient affective (emotional) state.

The task parsing handler 1080 receives task requests, determines specifications in each request, and creates an entry in the task specifications table 7000. A detailed description of the handler 1080 is given below with reference to FIG. 3.

The task completion handler 1120 updates the relevant entries in both the Task Specifications 7000 and Donor State 8000 tables. The task completion handler 1120 may also provide compensation to the relevant human resources. The detailed description of this handler 1080 is given below with reference to FIG. 3.

The server database 1140 in this exemplary embodiment provides for creation, deletion and modification of persistent data, and is used by the handlers 1060-1120 of the server 1000. In one embodiment of the current invention, the server database 1140 includes two tables, the task specifications table 7000 and the human resource state 8000 table, each depicted in FIGS. 7 and 8, respectively.

FIG. 7 illustrates an exemplary Task Specifications Table 7000 in accordance with the present invention. This table 7000 maintains the requirements and current state for each task supported by the server 1000. This table 7000 is an instance of a relational database table in which each row provides data about a particular task, and each column provides a particular type of specification or state data. The columns provide the following data about the tasks: Task ID (7010) is a unique identifier for the task (e.g., 321 (7090)), Work Location (7020) is an indication of where the human resources for this task will have to work (e.g., India (7100)), SLA (7030) indicates a Service Level Agreement such as, for example, the minimum level of service required (e.g., a "Gold" level of service (7110)), Current SL (7040) is the current level of service (e.g., Silver (7120)), Required Skills (7050) is a list of the skills a human resource must have to work on the job (e.g., Java and JSP (7130)), Number of Donors (7060) indicates the number of human resource required to complete the job (e.g., 30 (7140)), Job Length (7070) provides an estimate of how long the task will take to complete (e.g., 6 months (7150)), and Task Complete (7080) indicates whether or not the task is complete (e.g., no (7160)).

FIG. 8 depicts an exemplary human resource State Table 8000 in accordance with the present invention. The human resource State Table 8000 maintains information about a human resource that is supported by the server 1000. This information includes the affective and somatic state of the human resource as well as the availability and abilities of the human resource. Each row of this table holds the information about a particular human resource and each column holds a particular type of data. The columns indicate: Donor ID (8010) which is a unique ID for the human resource (e.g., 40960 (8100)), Blood Pressure (8020) which is the human resource's most recent blood pressure measurement (e.g., 110/80 (8110)), Pulse (8030) which is the human resource's most recent pulse reading (e.g., 70 (8120)), and Mood (8040) indicates the human resource's more recent mood (e.g., 8 (8130)). Methods of determining these values may include, for example, interviewing the human resource, self assessment by the human resource, as well as via biosensors that communicate with the human resource state update monitoring handler 1060.

The columns in the table 8000 further include Level of Fatigue (8050) that indicates the human resource's most recent level of fatigue (e.g., 2 (8140)), Acceptable locations (8060) that indicates work locations that are acceptable to the given human resource (e.g., US, India, UK (8150)), Skills (8070) that indicate the human resource's skill set (e.g., Java, JSP, REXX (8160)), Task ID (8080) which is the ID of the task to which the human resource is currently assigned ("None" if currently available, e.g., 321 (8170)), and SL Rating (8090) which indicates the level of service that was last provided by the human resource (e.g., Bronze (8170)). Note that this value may be initialized to the level of service last provided by the human resource in their previous task, or an average of the last level of service last provided by the human resource for all of their previous jobs.

The current invention also encompasses embodiments where the human resource State Table 8000 includes additional data such as, for example: a list of human resource (e.g., donor IDs) with whom a human resource is able to work, a list of human resources with whom a donor cannot work, a list of acceptable/unacceptable managers, and the like. Those of ordinary skill in the art understand that a human resource might actually be a set of human resources, a team, a department, or an organization (e.g., "the FooBar Company"). Thus, if a human resource's list of acceptable coworkers includes the "FooBar Company," then the human resource is able to work in projects which also include one or more FooBar employees.

Those of ordinary skill in the art understand that various implementations which store this type of data in multiple, possibly related—tables also falls within the scope of the current invention.

Figure 2:
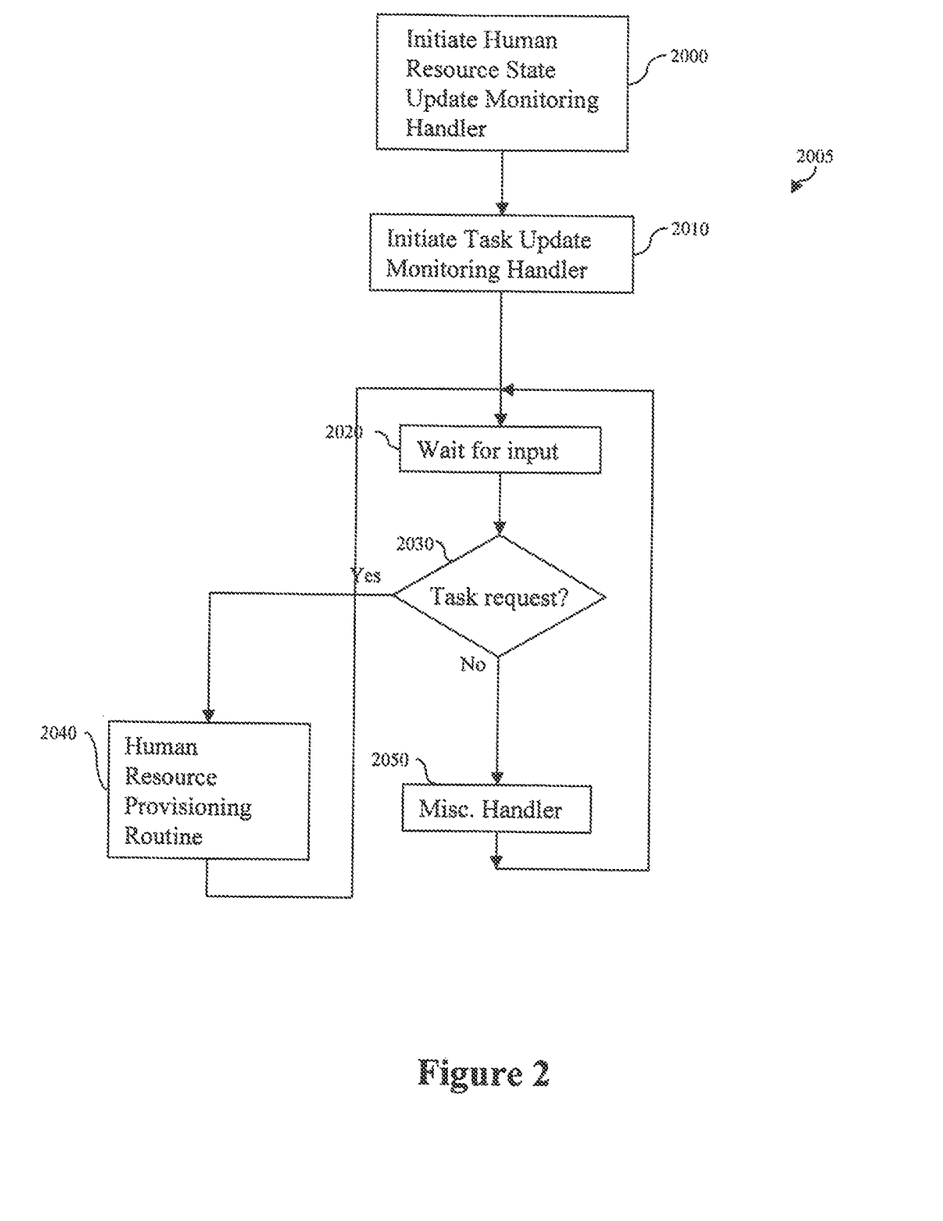
FIG. 2 is a flowchart 2005 of an exemplary method for optimizing utilization of human resources in accordance with the present invention.

FIG. 2 illustrates a flowchart 2005 of an exemplary control routine of the server's logic 1050. At step 2000, the human resource state update monitoring handler 1060 is started on the server 1000 to continuously capture and update the state of human resources. These updates are stored in the server database 1140. These updates and function of this handler are described in detail above with reference to FIG. 7. Those of ordinary skill in the art understand that the human resource state update monitoring handler 1060 may be run in a separate process on computer platforms such a Linux, as a separate thread in a Java program, or the like.

Next, in step 2010, the task state update monitoring handler 1070 is started on the server 1000 to continuously capture and update the state of a task, these updates are stored in the server database 1140. These updates and the function of this handler are both described above in detail with reference to FIG. 8.

Next, in step 2020, the server 1000 waits for inputs other than human resource and task state updates. When such an input is received, the server checks whether it is a request for a new task to be processed in step 2030. If the input is a request for a new task, then, in step 2040, the server 1000 initiates an instance of a human resource Provisioning Routine that is described in detail below with reference to FIGS. 3-6. Following this, the control routine returns step 2020. If, however, in step 2030, the server 1000 determines that the input is not a new task processing request, then a miscellaneous handler (not shown) may be invoked in step 2050 and the control routine returns to step 2020.

Figure 3:
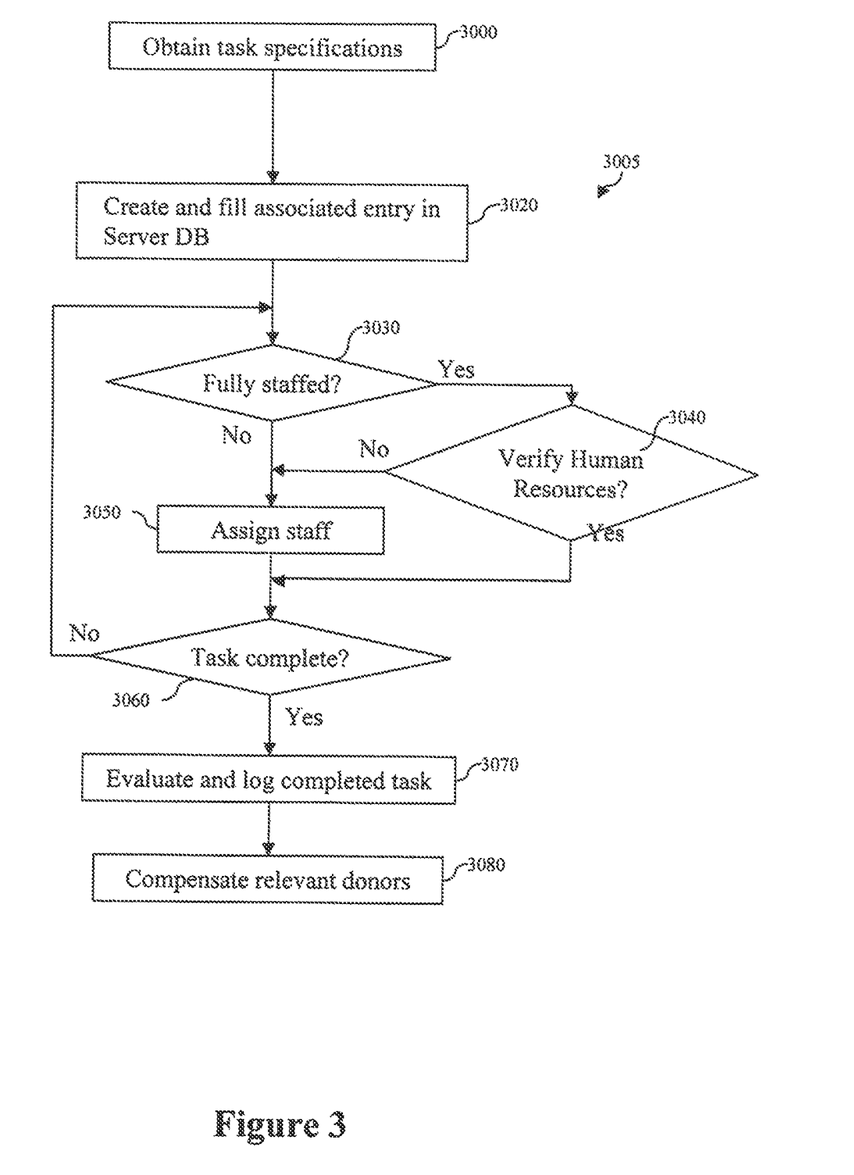
FIG. 3 is a flowchart 3005 of an exemplary method for optimizing allocation of human resources in accordance with the present invention.

FIG. 3 illustrates a flowchart 3005 of an exemplary human resource Provisioning Routine. This routine assigns and constantly verifies that sufficient donors are assigned to given task until the task has been completed, the sufficiency including skill level, work quality level, somatic (physical) state, and affective (emotional) state. This routine is invoked by the Server 1000 whenever a new task request is received (step 2040). At step 3000, the task parsing handler 1080 is invoked to obtain all of the specifications of the task. These include, for example, a description of: where the work must be done, an estimate of how long the work will take, any service level requirements (SLA's), an estimate of how many donors will be required, the skills required of each of these human resources, and the like.

Once obtained, the task parsing handler 1080, in step 3020, updates the task specifications table 7000 to hold these requirements. This includes, for example: creating a new entry in the task specifications table 7000, creating a new (unique) ID for the task, and then entering all of the specifications of the new task into column cells, in the case of relational-DB task specifications table 7000.

When complete, in step 3030, the server 1000 checks whether the given task is fully staffed—clearly false the first time this value is checked for a given task. This check can be accomplished by first determining the estimated number of required human resource s7140 from the task specifications table 7000, and then comparing this to the total number of human resources assigned to the given task (i.e., those whose task ID (8170) that matches the task ID 7090 in the task specifications table 7000.

If the task has not been sufficiently staffed, then, in step 3050, the human resource assigning handler 1090 is invoked, which will be described in detail below with reference to FIG. 4. Following this, the state of the given task is checked in step 3060 to determine whether the task has been completed. In one embodiment of the current invention, this is accomplished by checking the task complete values 7080 for the given task in the task specifications table 7000. For example, the task complete value 7160 for task 321 (7090) is "no."

If, in step 3060, the system 1000 determines that the task is not complete, then the control routine returns to step 3030. If, however, in step 3060, the system determines that the task is complete then the control routine continues to step 3070 where the task completion handler 1120 is invoked. This handler 1120 both evaluates how the given task (e.g., 321) was completed and updates any and all relevant tables in the Server database 1140. These updates may include updates to the task specifications table 7000 (e.g., the task is now complete) and relevant entries in the human resource state table 8000, including the fact that all human resources previously assigned to the given task are now available. Human resource state table updates may also include indications of how well each relevant human resource performed. Finally, in step 3080, the task completion handler 1120 provides all relevant human resources with the appropriate compensation for their work.

If, in step 3030, the server 1000 determines that the task is fully staffed, then the control routine continues to step 3040 where the human resource verifying handler 1100 (described in detail below with reference to FIG. 5) is invoked. This handler 1100 determines and returns whether or not all of the human resources currently assigned to the given task are still compatible with the task. If the handler 1110 determines that the human resources are not compatible, then the control routine continues to step 3050 where the human resource assigning handler 1100 is called to assign sufficient staff. Otherwise, the control routine continues to step 3060, in which the server 1000 determines whether the given task has been completed.

Figure 4:
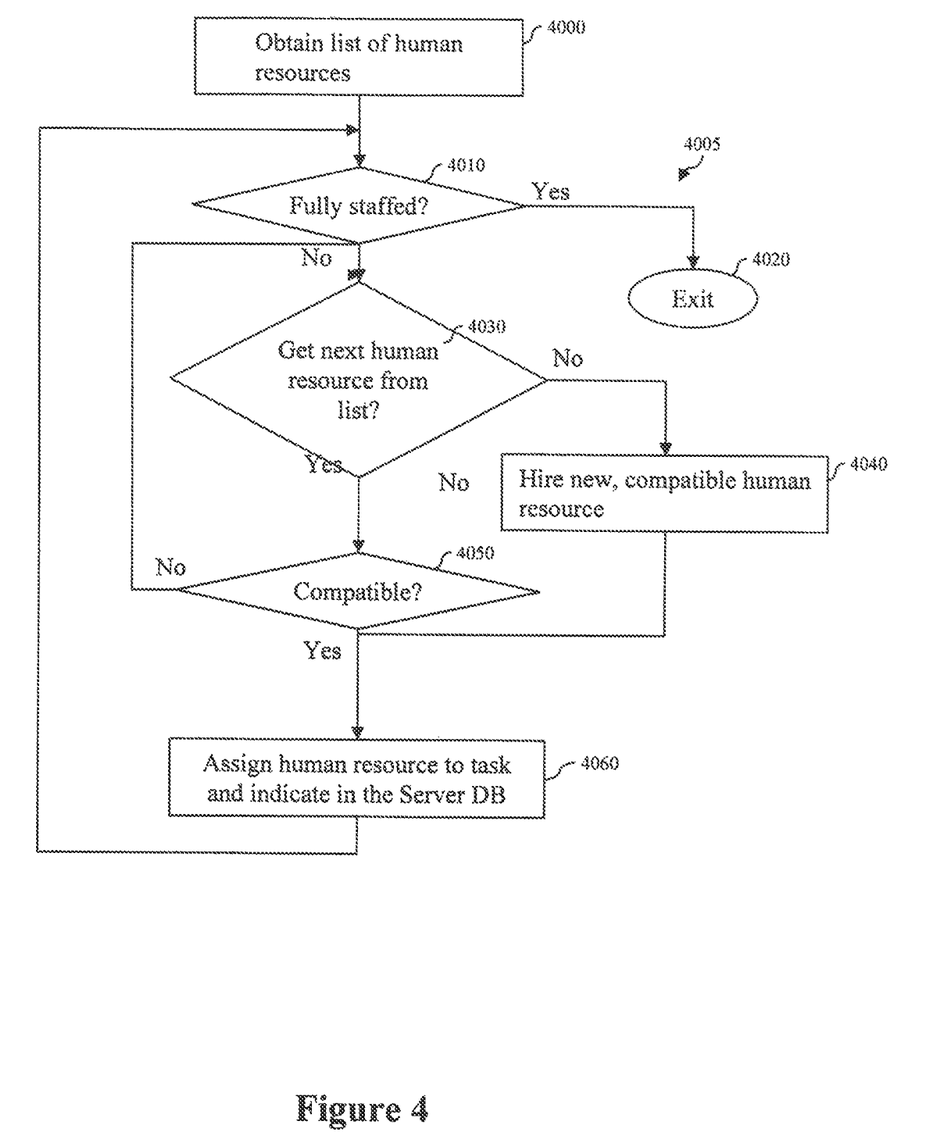
FIG. 4 is a flowchart 4005 of an exemplary method for assigning human resources in accordance with the present invention.

FIG. 4 illustrates an exemplary flow chart for the human resource assigning handler 1090 in accordance with the present invention. This handler 1090 assigns sufficient donors for a given task. The flowchart starts at step 4000 where the handler 1090 obtains a list of all potential human resources (e.g., by obtaining a list of all human resource IDs 8010 from the human resource state table 8000). Next, in step 4010, the handler 1090 determines whether a sufficient number of human resources have been assigned to the given task. This may be accomplished by determining whether the number of human resources that are currently assigned (e.g., the number of entries in the human resource state table whose task ID value 8080 equals the ID of the task e.g., 321) is equal to the number of human resources 7060 from table 7000 that are required for the task (e.g., 30 (7140) for task 321). If so, then the control routine ends at step 4020.

If, however, the handler 1090 determines that a sufficient number of human resources have not been assigned, then the control routine continues to step 4030. In step 4030, the handler 1090 reads the next human resource ID from the list of potential human resources. If no such human resource ID remains, then the control routine continues to step 4040 where the new hire handler 1130 is invoked (described in detail below with reference to FIG. 9) to obtain an additional human resource. Following this, control routine continues to step 4060.

If, however, in step 4030 an existing human resource ID is available, then the compatibility of this human resource to the given task is determined in step 4050. This may be accomplished using the compatibility verifying handler 1110 (described in detail below with reference to FIG. 6). If the human resource is not compatible with the task, then the control routine continues to step 4030. If the human resource is compatible with the task, then in step 4060, the human resource is assigned to the task. In an exemplary embodiment of the current invention, this is accomplished by setting the task ID 8080 for the human resource in the donor state table 7000 to that of the task. For example, as shown in FIG. 8, the human resource with donor ID 40960 (8100) has their task ID set to 321 (8170).

Figure 5:
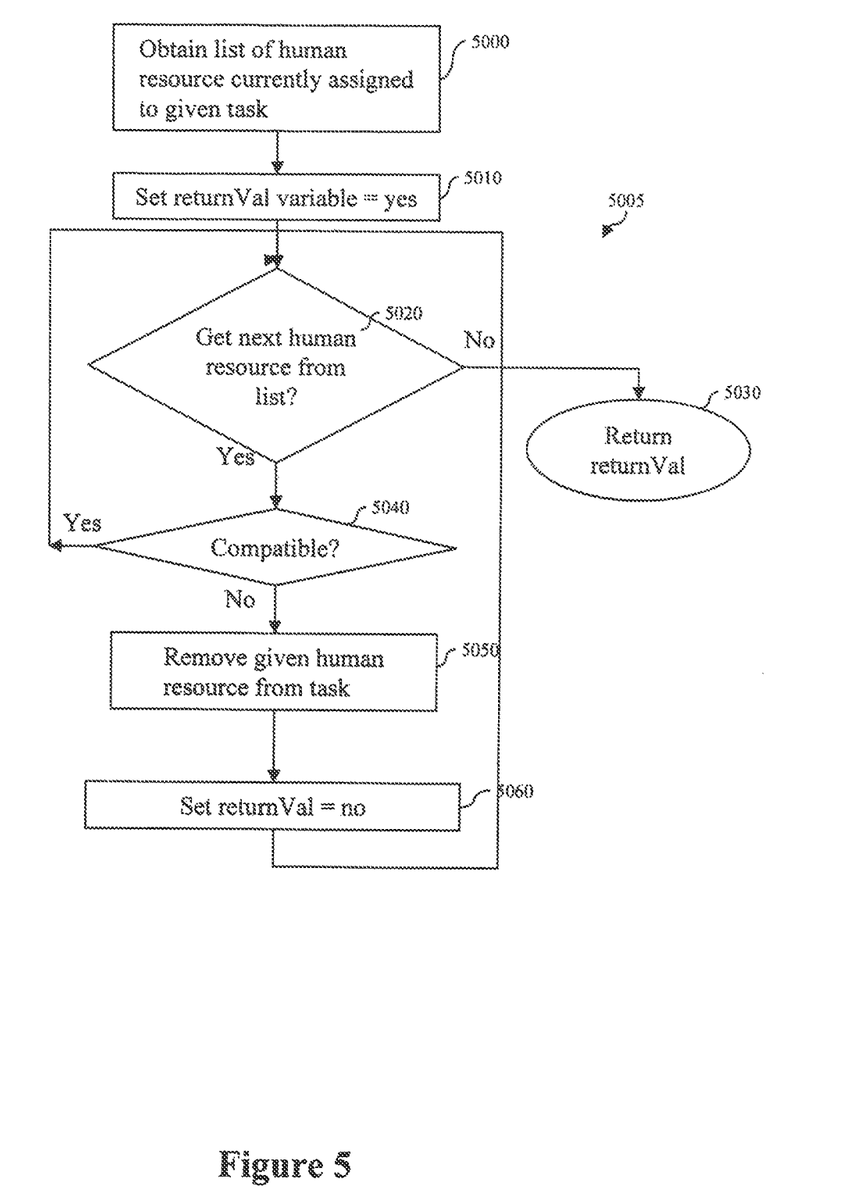
FIG. 5 is a flowchart 5005 of an exemplary method for verifying agent assignments in accordance with the present invention.

FIG. 5 illustrates a flow chart of an exemplary control routine of the human resource verifying handler 1100. This handler 1100 verifies and determines whether all of the human resources currently assigned to a task are still compatible with that task. At step 5000 the handler 1100 generates a list of all of the human resources currently assigned to the given task (e.g., task ID 321). This may be accomplished by finding the donor ID 8010 of all of the human resources whose task ID value 8080 in the human resource state table 8000 equals the ID of the task (e.g., 321). Next, in step 5010, a local variable, "returnVal" is set equal to "yes." Next, in step 5020, the handler 1100 reads the next human resource ID from the list of human resources currently assigned to the task from the human resource state table 8000. If no further human resource IDs are available (i.e., if all of the human resource IDs initially retrieved in step 5010 have already been processed) then value of the "returnVal" variable is returned in step 5030. If, however, another human resource ID is read from the donor list, then, in step 5040, the human resource verifying handler 1100 invokes the human resource compatibility handler 1110 (described in detail below with reference to FIG. 6) to determine whether the human resource associated with the human resource ID is still compatible with the task (both the user ID and task ID being passed to the human resource compatibility handler 1110). If the human resource is still compatible, then the control routine continues to step 5020. If, however, the human resource is not compatible with the task, then, in step 5050, they are unassigned from the task. In an exemplary embodiment of the current invention, this may be accomplished by changing the task ID value 8170 from that of the task to "none." For example, for the human resource with donor ID 40960 (8100) the value of the 8170 cell may be changed from "321" to "none." Following this, the value of "returnVal" is set to "no," in step 5060, to indicate that all of the human resources that were assigned to the task are not compatible with it. Following this, control routine returns to step 5020.

Figure 6:
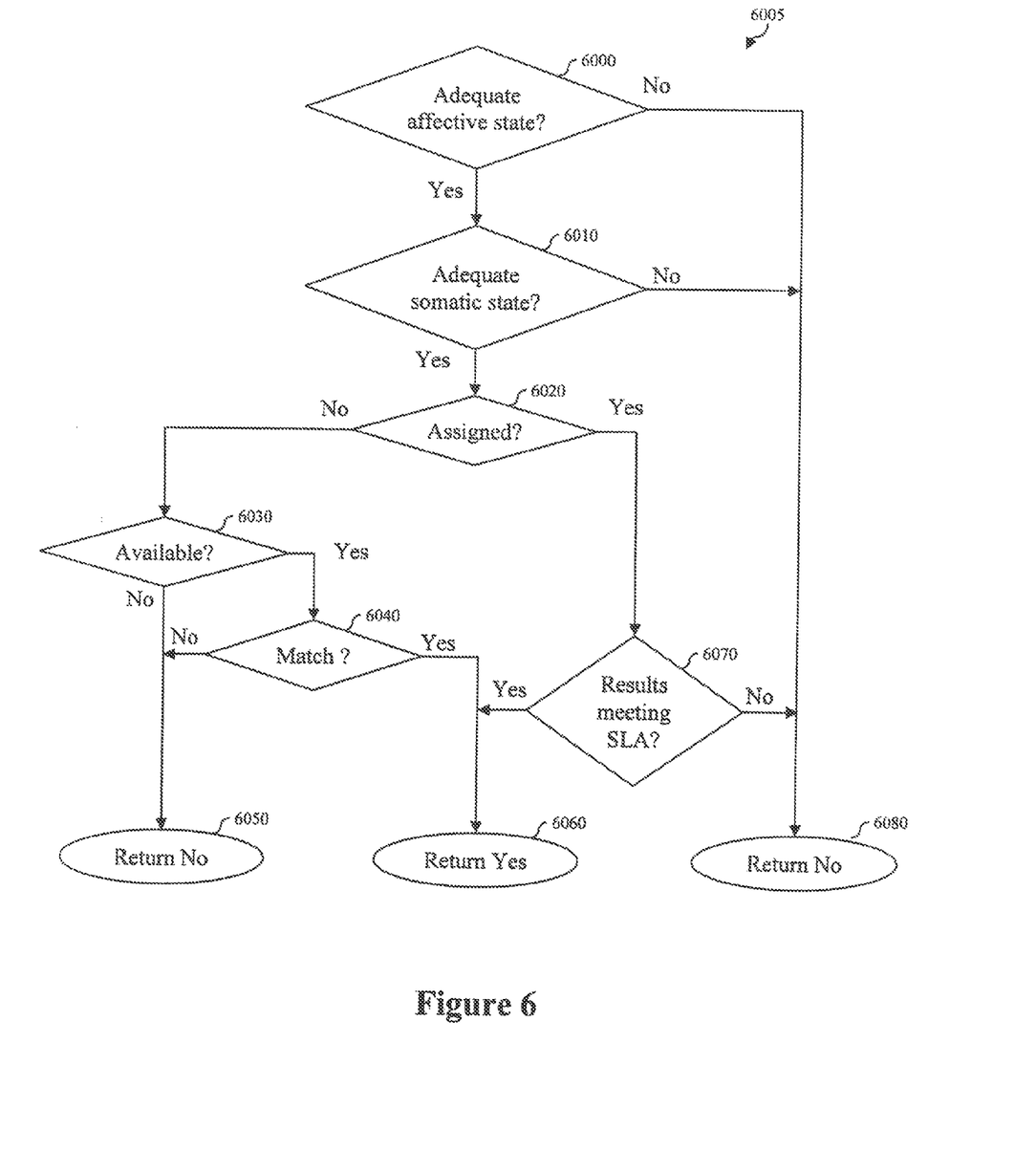
FIG. 6 is a flowchart 6005 of an exemplary method for checking compatibility of a human resource with a task in accordance with the present invention.

FIG. 6 illustrates a flow chart 6005 of a control routine of the human resource compatibility handler 1110. For each execution, this handler 1110 receives the ID of a human resource (e.g., 40960) and the ID of a task (e.g., 321). Each of the values checked below are from the row of the human resource State Table 8000 that matches the human resource ID, and from the row of the State Specifications Table 7000 that matches the task ID. Thus, for example, for human resource ID=40960, this is row 8190 and for task ID=321 this is row 7170.

The handler 1110 also holds a set of acceptable threshold values for particular table cells. These thresholds are used to determine whether a current value is adequately high. At step 6000, the handler 1110 determines whether the human resource is in an adequate affective (emotionally related) state. In one embodiment of the current invention, this is accomplished by checking first that the human resource's mood 8040 is sufficiently high, e.g., that the value 8130 is not below the handler's 1110 mood threshold value (e.g., 6). Next, in step 6000, the handler 1110 determines whether the human resource's level of fatigue is beyond a fatigue threshold value (e.g., 2). If either of the above checks fails, then the control routine continues to step 6080 where the handler 1110 returns a value of "No."

Otherwise, in step 6010 the handler 1110 checks whether the human resource's somatic (physical) state is adequate. In one embodiment of the current invention, this is accomplished by making two checks, the first being whether the human resource's blood pressure 8020 is within an acceptable threshold range. In the case of human resource ID 40960 (8100 in table 8000), this check passes because the human resource's value of 110/80 (8110) turns out to meet the handler's 1110 requirements (e.g., above 80/50 and below 200/100). The other check is whether the human resource's pulse rate, 70 (8102) is adequate (e.g., a threshold range of greater than 50 and less than 200). If the somatic state check were to fail, then the control routine continues to step 6080 where the handler 1110 would return "No." Otherwise, the control routine continues to step 6020.

In step 6020, the handler 1110 determines whether the human resource (human resource ID=40906) is assigned to the task (e.g., task ID=321). In one embodiment of the current invention, this is accomplished by verifying that the task ID (e.g., 321) matches the task ID 8080 for the human resource (e.g., table cell 8170 for the user with ID 40960). If this check succeeds (i.e., the donor is assigned to the task) then the control routine continues to step 6070 where the handler 1110 determines whether the service level of the human resource is adequate for the task. In one embodiment, this is accomplished by verifying that the human resource's current SL Rating 8090 ("Bronze" 8180 in the case of the human resource with human resource ID 40960) meets or beats the task's SLA value 7030 ("Gold" 7110 in the case of the task with ID=321). If this check 6070 succeeds, then the control routine continues to step 6060. In step 6060, the handler 1110 returns "yes."

If, however, in step 6020 the handler 1110 determines that the human resource is not assigned to the task, then the control routine continues to step 6030. In step 6030, the handler 1110 determines whether the human resource is currently available. In one embodiment, this is accomplished by verifying that the value of the human resource Task ID 8080 is "None." If not, the control routine continues to step 6050 and the handler 1110 returns "no." If, however, in step 6030, the handler 1110 determines that the human resource is available, then the control routine continues to step 6040. In step 6040, the control routine determines whether the human resource's other state data match the task. This includes check that the human resource skill set 8070 contains at least those skills specified by the task's required skills 7050. It also includes verifying that the human resource's Acceptable Locations set 8060 contains the location that is specified by the task's Work Location value 7020. If, however, the control routine determines that the human resource's state data does not match the task, then the control routine continues to step 6050.

Figure 9:
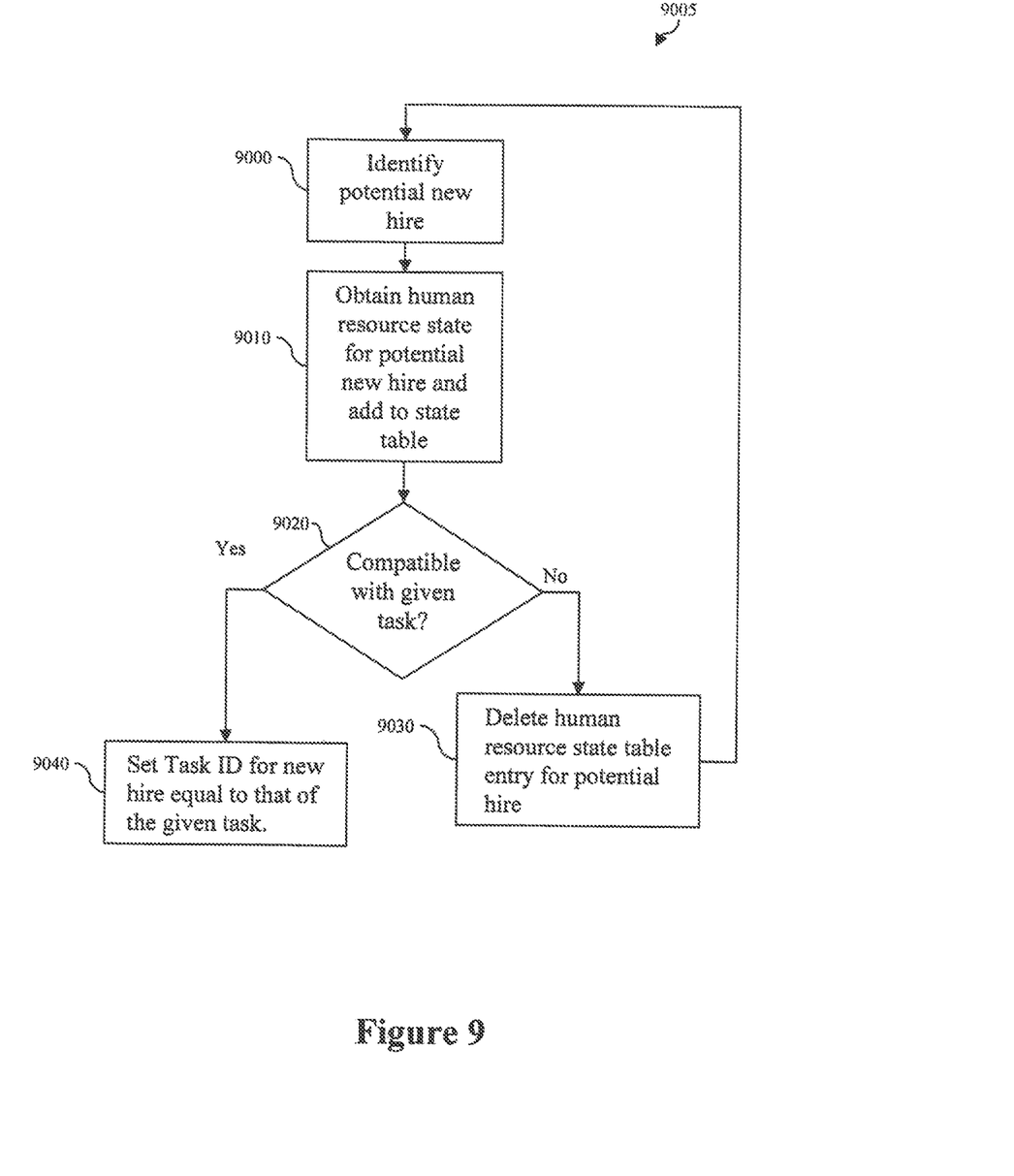
FIG. 9 is a flowchart 9005 of an exemplary method for handling new hires in accordance with an exemplary embodiment of the present invention.

FIG. 9 is an exemplary flow chart 9005 of a control routine for the new hire handler 1130. For each execution, this handler 1130 receives the ID of a task (e.g., 321). The handler 1130 identifies and adds a new human resource that is compatible with the task. In step 9000, the handler 1130 identifies a candidate human resource that may be compatible with the task. In step 9010, the handler 1130 obtains all of the needed state information about the candidate human resource. This information may include all of the data that is needed for a human resource State Table 8000 (i.e., blood pressure 8020, pulse 8030, mood 8040, acceptable work locations 8060, skills 8070, and an indication of the service level rating they are able to provide 8090). Means of retrieving this information include, for example, documents (e.g., a resume), interviews, and testing by a registered healthcare worker (e.g., a nurse). Given all of this data, the handler 1130, creates a new entry in the human resource State Table 7000 for the candidate human resource and sets the Task ID 8080 to "None."

Next, in step 9020, the handler 1130 invokes the human resource compatibility handler 1110, by passing human resource compatibility handler 1110 the human resource's ID and the ID of a task, to determine if the candidate human resource is compatible with the task. If the human resource compatibility handler 1110 returns a "yes," then the control routine continues to step 9040. In step 9040, the new hire handler 1130 sets the candidate human resource's Task ID 8080 to the ID of the Task, indicating that the candidate human resource is assigned to the task. If, however, in step 920, the human resource compatibility handler 1110 returns a "no," then the control routine continues to step 930 where the new hire handler 1130 deletes the entry for the candidate human resource from the human resource State Table 7000. The control routine then returns to step 9000.

Those of ordinary skill in the art understand that a first user, e.g., a service organization, may provide the current invention for a second user, e.g., a customer organization. This may require the first user to maintain a server 1000 for the second user, maintain all of the state information—task and human resource—for the second user's tasks and human resources, allow the customer organization to specify new task requests, and maintain the staff for any and all such task requests until completed.

Those of ordinary skill in the art also understand that a first user, e.g., a service organization may provide the function of the human resource compatibility handler 1100 for a second user, e.g., a customer organization. This may require the first user to either maintain a server 1000 for the second user, or to access a server 1000 maintained by the second user's. The first user would then be responsible for determining and returning the compatibility of any given user and task pair (i.e., whether the given user is currently compatible with the given task).

Those of ordinary skill in the art will further understand that a first user, e.g., a service organization may provide the function of the human resource verifying handler 1110 for a second user, e.g., a customer organization. This may require the first user to either maintain a server 1000 for the second user, or to access a server 1000 maintained by the second user's. The first user would then be responsible for determining and returning whether all human resources currently assigned to a given task are compatible with it.

Figure 10:
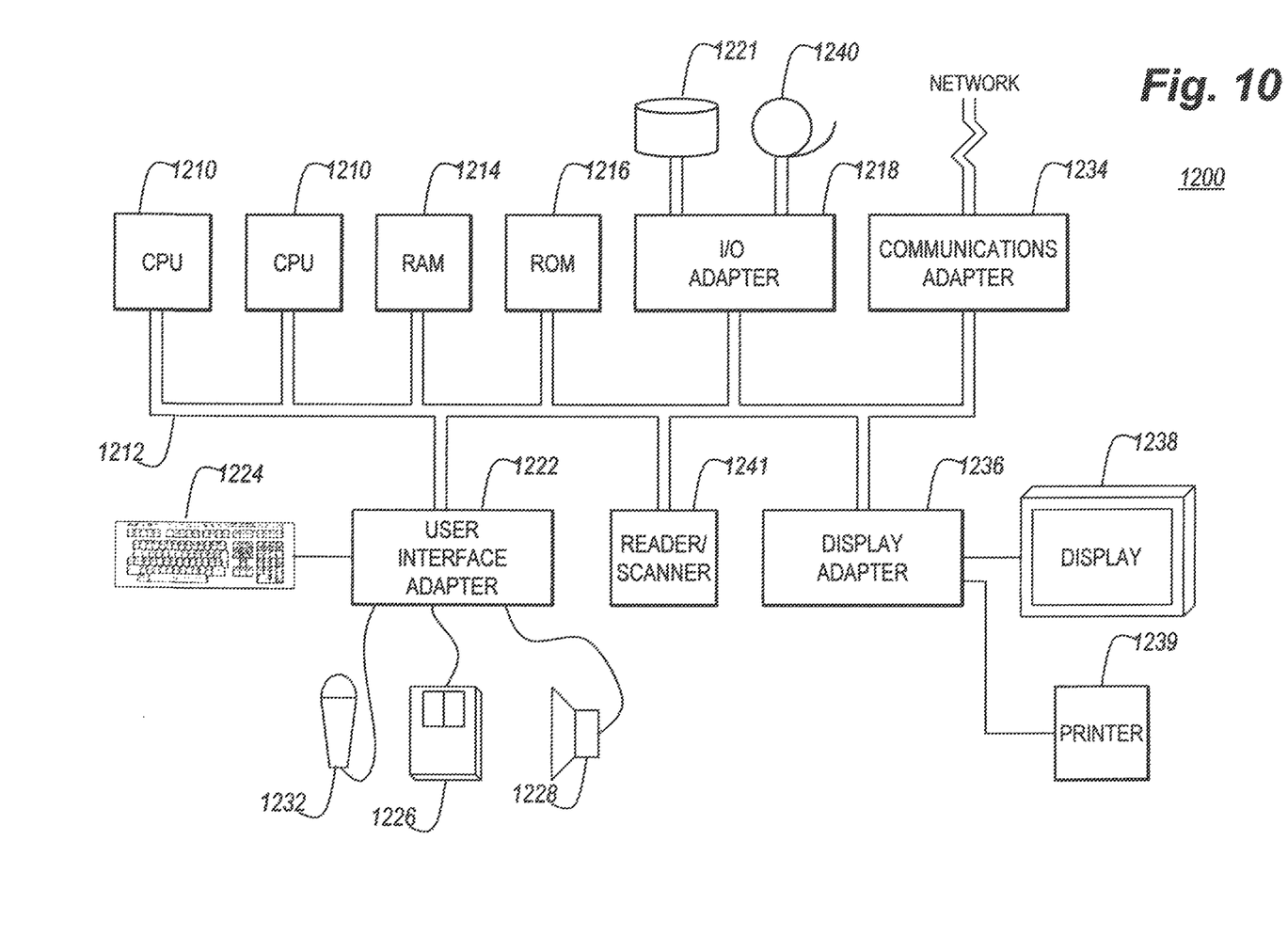
FIG. 10 illustrates an exemplary hardware/information handling system 1200 for incorporating the present invention therein.

FIG. 10 illustrates a typical hardware configuration of an information handling/computer system 1200 for use with the invention and which preferably has at least one processor or central processing unit (CPU) 1211.

The CPUs 1211 are interconnected via a system bus 1212 to a random access memory (RAM) 1214, read-only memory (ROM) 1216, input/output (I/O) adapter 1218 (for connecting peripheral devices such as disk units 1221 and tape drives 1240 to the bus 1212), user interface adapter 1222 (for connecting a keyboard 1224, mouse 1226, speaker 1228, microphone 1232, and/or other user interface device to the bus 1212), a communication adapter 1234 for connecting an information handling system to a data processing network, the Internet, an Intranet, a personal area network (PAN), etc., and a display adapter 1236 for connecting the bus 1212 to a display device 1238 and/or printer.

In addition to the hardware/software environment described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

This signal-bearing media may include, for example, a RAM contained within the CPU 1211, as represented by the fast-access storage for example. Alternatively, the instructions may be contained in another signal-bearing media, such as a magnetic data storage diskette 1300 (FIG. 11), directly or indirectly accessible by the CPU 1211.

Figure 11:
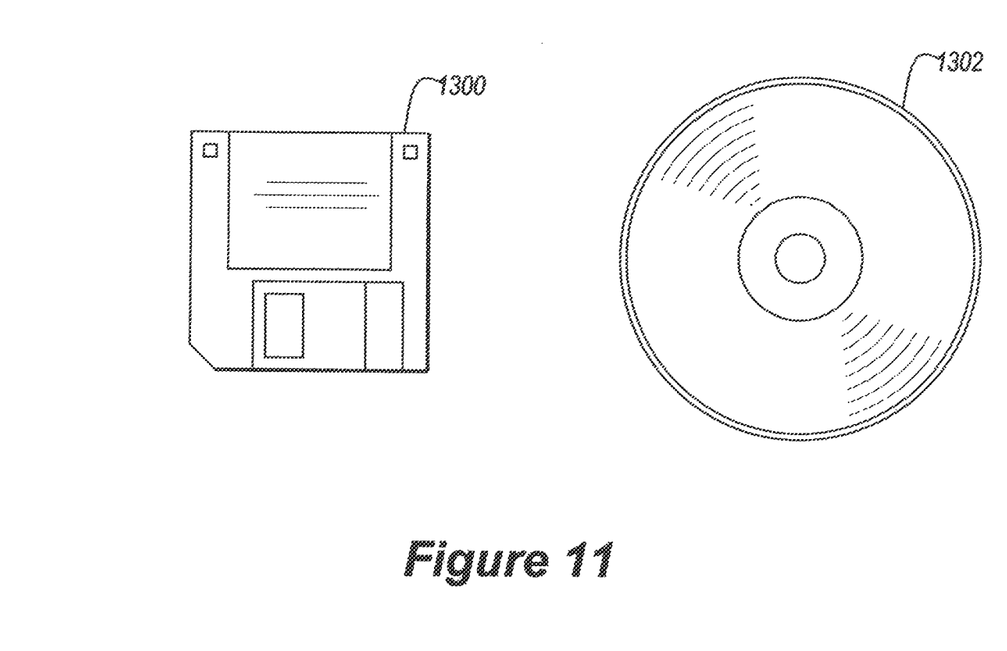
FIG. 11 illustrates signal bearing media 1300 and 1302 (e.g., storage medium) for storing steps of a program of a method according to the present invention.

Whether contained in the diskette 1300, the computer/CPU 1211, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g. CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code, compiled from a language such as "C", etc.

The evolution of Internet-based services is reflected in designations that commonly reflect software upgrades. The first "version" of the Internet has been labeled "Web 1.0." Web 1.0 was mainly the Internet of free information access, for example via portals and newsgroups. Easy to remember domain names secured success. For a surfer it was imperative to be online.

The current version of the Internet is called "Web 2.0." Web 2.0 is the Internet of free information production. Millions of web users present their thoughts, impressions and experience in form of text, videos, photos and podcasts to the global web community. Social Networks are the key success factor for Web 2.0 applications. To survive in a social net, it is imperative for a participant to gain a high ranking by a search engine or a high ranking within a social network.

The next version of the Internet is being designated "Web 3.0." Web 3.0 is the web of semantics. In a semantics Web, each action has one or several counteractions within a complex system. If an individual, a group or a region is out-of-balance, intelligent counteractions within the web will make sure that the affected part can reach again the equilibrium or the pareto optimum as it is called in an economical system. The semantics web at least makes sure that parts in order are not getting out of control. In such a system it is imperative that enterprise information and market information is completely transparent to make sure the whole system survives. Not the knowledge of individuals will be of societal value, but their creativity.

An exemplary embodiment of the present invention may be implemented as a "Web 3.0" solution. This embodiment seeks an equilibrium of the healthiness and wealthiness on each level of a system from the individual level, to the organization level, and up to the world community level. The pareto optimum is based upon the welfare of each and everyone and is not only based upon monetary principles. In this manner, optimum state creativity may flourish.

While the invention has been described in terms of several exemplary embodiments, those skilled in the art will recognize that the invention can be practiced with modification.

Further, it is noted that, Applicants' intent is to encompass equivalents of all claim elements, even if amended later during prosecution.

What is claimed is:

1. A method for optimizing utilization of a human resource, said method comprising:
   determining an emotional state and a physical state of said human resource;
   determining, using a computer processor, whether the emotional state and the physical state of said human resource correspond to a task;
   determining a desired stimulation zone, wherein said determining the emotional state and the physical state of said human resource comprises:
      receiving data input by said human resource describing at least one of the emotional state and the physical state; and
      receiving data from a non-invasive sensor worn by said human resource, and
   wherein said determining the emotional state further comprises determining an amount of stimulation of said human resource, and evaluating whether said human resource is balanced into the desired stimulation zone by a grid computing model which imbeds said human resource as a central resource; and
   determining whether a current workload of said human resource, a skill set of said human resource, an output of said human resource, a production rate of said human resource, an accuracy rate of said human resource, a compatibility with co-workers of said human resource, personal preferences of said human resource, and a location corresponds to said task.

2. The method of claim 1, wherein said determining the emotional state and the physical state further comprises monitoring the emotional state and the physical state of said human resource.

3. The method of claim 1, wherein the emotional state and the physical state are modeled as a tuple where each element of said tuple indicates a level of the emotional state and the physical state.

4. The method of claim 1, wherein said human resource comprises a plurality of humans.

5. The method of claim 1, wherein said determining the emotional state and the physical state further comprises determining the emotional state and the physical state for each of a plurality of human resources, and
    wherein said determining whether the emotional state and the physical state correspond to a task comprises determining whether the emotional state and the physical state for at least one of the plurality of human resources corresponds to said task.

6. The method of claim 1, further comprising analyzing usage patterns of said human resource.

7. The method of claim 1, further comprising:
    allocating said human resource to said task; and
monitoring the execution of said task by said human resource.

8. The method of claim 7, further comprising determining whether the execution of said task by said human resource meets a service level agreement for said task.

9. The method of claim 1, further comprising modeling said human resource as a multi-dimensional state system based upon the emotional state and the physical state of said human resource.

\* \* \* \* \*